US00PP37752P3

(12) United States Plant Patent
Olesen

(10) Patent No.: US PP37,752 P3
(45) Date of Patent: Oct. 13, 2026

(54) MINIATURE ROSE PLANT NAMED 'Poulpar137'

(50) Latin Name: *Rosa hybrida*
Varietal Denomination: Poulpar137

(71) Applicant: Mogens Nyegaard Olesen, Fredensborg (DK)

(72) Inventor: Mogens Nyegaard Olesen, Fredensborg (DK)

(73) Assignee: POULSEN ROSER ALS, Fredensborg (DK)

( * ) Notice: Subject to any disclaimer, the term of this patent is extended or adjusted under 35 U.S.C. 154(b) by 54 days.

(21) Appl. No.: 18/831,805

(22) Filed: Sep. 15, 2025

(65) Prior Publication Data

US 2026/0083031 P1 Mar. 19, 2026

(30) Foreign Application Priority Data

Sep. 19, 2024 (QZ) ..... PBR 20242192

(51) Int. Cl.
*A01H 5/02* (2018.01)
*A01H 6/74* (2018.01)

(52) U.S. Cl.
USPC ..... Plt./119
CPC ..... *A01H 6/749* (2018.05); *A01H 5/02* (2013.01)

(58) Field of Classification Search
USPC ..... Plt./101, 116, 119
See application file for complete search history.

(56) References Cited

U.S. PATENT DOCUMENTS

2014/0373208 P1 * 12/2014 Olesen ..... A01H 6/749 Plt./118

* cited by examiner

*Primary Examiner* — Karen M Redden

(57) ABSTRACT

A new garden rose plant of the miniature class which has abundant, yellow-orange flowers and attractive foliage. This new and distinct variety has shown to be uniform and stable in the resulting generations from asexual propagation.

1 Drawing Sheet

Botanical designation: *Rosa hybrida.*

Variety denomination: 'Poulpar137'.

This application claims priority to Plant Breeder's Rights Application Number 2024/2192, which was filed at the Community Plant Variety Rights Office in the European Union on Sep. 19, 2024, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2019 and the resulting seeds were planted in a controlled environment in Fredensborg, Denmark. The new variety, named 'Poulpar137', originated as a single seedling from the stated cross.

The new variety may be distinguished from its male pollen parent and female seed parent primarily by the following characteristics. The male pollen parent plant has orange red flowers while the new variety has yellow-orange flowers. The female seed parent plant has light yellow flowers while the new variety has yellow-orange flowers.

The objective of the hybridization of this rose variety was to create a new and distinct variety with unique qualities, such as:

1. Uniform and abundant yellow-orange flowers with long shelf-life;
2. Vigorous, but compact growth when propagated on its own roots;
3. Suitability for commercial production in small containers; and
4. Exceptional disease resistance.

This combination of qualities is not present in previously available commercial cultivars of this type, known to the inventor, and distinguish 'Poulpar137' from all other varieties of which we are aware.

As part of the rose development program, Mogens N. Olesen germinated the seeds from the aforementioned hybridization during winter of 2019 and conducted evaluations on the resulting seedlings in a controlled environment in Fredensborg, Denmark. 'Poulpar137' was selected in the spring of 2020 by the inventor as a single plant from the progeny of the aforementioned hybridization.

Asexual reproduction of 'Poulpar137' by rooted cuttings was first done by Mogens N. Olesen in the nursery in Fredensborg, Denmark in July 2020. This initial and other subsequent asexual propagations conducted in controlled environments have demonstrated that the characteristics of 'Poulpar137' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar137'. Specifically illustrated in the drawing are open flowers viewed from above and the side, a cluster of flowers on a branch, sepals and flower petals detached revealing reproductive flower parts, a portion of bare stem, mature and juvenile leaves. Plants shown in the drawing are 3 months of age.

DETAILED DESCRIPTION OF THE VARIETY

The following is a description of 'Poulpar137', as observed in its growth in an indoor glasshouse nursery in Odense Denmark. Observed plants are 3 months of age, and were grown on their own roots in 17 cm pots. Color references are made using The Royal Horticultural Society (London, England) Colour Chart, 2001, except where common terms of color are used.

For a comparison, several physical characteristics of the rose variety 'Poulty015', U.S. Plant Pat. No. 26,017 are compared to the claimed plant. While 'Poulpar137' has 43 flower petals, 'Poulty015' has 75 flower petals. The claimed plant has grows to a height of 26 cm while 'Poulty015' grows to a height of about 16 cm. Open flowers of 'Poulpar137' are generally Yellow-Orange Group 16A with intonations of Orange Group 25B in color while 'Poulty015' has a general tonality of Yellow Group 10C with intonations of Yellow-Orange Group 23C.

Flower and Flower Bud

Blooming habit: Continuous.

Flower bud:

- *Size.*—Upon opening, 26 mm in length from base of receptacle to end of bud. Bud diameter is 19 mm.
- *Bud form.*—Ovoid.
- *Bud color.*—As sepals divide petals are Yellow-Orange Group 14C and Orange Group 25C.
- *Sepal inner surface.*—Color: Yellow-Green Group 146D. Surface: Lightly pubescent.
- *Sepal outer surface.*—Color: Yellow-Green Group 144A. Texture: Smooth.
- *Sepal shape.*—Apex: Cirrhose. Base: Flat at union with receptacle.
- *Sepal margin.*—Margins have no foliaceous appendages on three of the five sepals.
- *Sepal size.*—About 23 mm long, 9 mm wide.
- *Receptacle.*—Texture: Smooth. Size: 6 mm in height, 10 mm wide. Color: Yellow-Green Group 144A. Shape: Funnel.
- *Pedicel.*—Surface: Pubescent. Length: 38 mm on average. Diameter: 2.5 mm on average. Color: Yellow-Green Group 144A. Strength: Strong.
- *Peduncle.*—Length: Variable from 15 to 25 mm. Diameter: About 4 mm. Color: Yellow-Green Group 144A. Texture: Smooth. Strength: Very strong.

Flower bud development: Flower buds are borne either singly or in clusters of about 5 flower buds per stem.

Flower bloom:

- *Fragrance.*—Light floral scent.
- *Duration.*—The blooms have a duration on the plant of approximately 21 days. Petals fall cleanly away from plant after flowers have fully matured.
- *Size.*—Flower diameter is 55 mm when open. Flower depth is 22 mm.
- *Flower shape.*—Broad and open cup, double flower, with petals that curve out from the center.
- *Shape of flower, side view.*—The upper portion is convex. The lower portion is flat.

Petalage: Under normal conditions, flowers have about 43 petals.

General tonality of flower: Open flowers are Yellow-Orange Group 16A with intonations of Orange Group 25B. After 10 days Yellow Group 10C with intonations of Yellow-Orange Group 22D.

Petal color:

- *Upon opening, outer petals.*—Upper surface: Yellow-Orange Group 15A with occasional streaks of Yellow-Orange Group 22B. Lower surface: Yellow Group 12B with streaks of Orange Group 26A and Yellow-Orange Group 22A.
- *Upon opening, inner petals.*—Upper surface: Yellow Orange Group 15B. Lower surface: Yellow Group 13A with streaks of Orange Group 26A.
- *Basal petal spots, upon opening.*—Upper surface: Yellow Group 12A. Lower surface: Yellow Group 12A.
- *After opening, outer petals.*—Upper surface: Shades of Yellow Group 12A and Yellow-Orange Group 15C at the basal and middle zone. The marginal zone is Yellow-Orange Group 18C. Lower surface: Yellow Group 8A with streaks of Yellow-Orange Group 20A. Marginal Orange Group 29C.
- *After opening, inner petals.*—Upper surface: Yellow Group 12A and towards margins Yellow-Orange Group 15B. Lower surface: Yellow Group 12A at the basal zone. Margins are Orange Group 24A.
- *Basal petal spots, after opening.*—Upper surface: Yellow Group 8A. Lower surface: Yellow Group 8A.

Petals:

- *Petal reflex.*—Lightly reflexed.
- *Margin.*—Entire and uniform. No undulations.
- *Shape.*—Broad and elliptic. Apex shape: Rounded. Base shape: Acute.
- *Size.*—26 mm (l)×30 mm (w).
- *Texture.*—Smooth.
- *Thickness.*—Average.

Petaloids:

- *Size.*—14 mm (l) by 6 mm (w).
- *Quantity.*—About 10.
- *Shape.*—Elliptical with an acute base and rounded apices.
- *Color.*—The upper surface is Yellow Group 12A with marginal intonations of Yellow-Orange Group 15B. The lower surface is Yellow Group 12A with marginal intonations of Orange Group 24A.

Reproductive flower parts:

- *Pollen.*—None observed.
- *Anthers.*—Size: 2 mm in length. Color: Yellow-Orange Group 19D. Quantity: 65 on average.
- *Filaments.*—Color: Yellow Group 9A. Length: 6 mm.
- *Pistils.*—Length: 10 mm. Quantity: 60 on average.
- *Stigmas.*—Color: Greyed-Yellow Group 160 A.
- *Styles.*—Color: White Group 155 A with intonation of Red Group 52C.
- *Location of stigmas.*—Even in location relative to the length of the filaments and the height of the anthers.
- *Hips.*—None Observed.

Plant

Plant growth: Upright. Plants are about 26 cm in height, and 28 cm wide.

Stems:

- *Color of juvenile growth.*—Yellow-Green Group 144B.
- *Color of mature growth.*—Yellow-Green Group 146B.

*Length*.—Canes are about 15 cm from the base of the plant to the flowering portion.

*Diameter*.—About 4.5 mm.

*Internodes*.—On mature canes about 20 to 30 mm between nodes.

*Surface texture*.—Young wood: Smooth. Older wood: Smooth, somewhat glaucous.

Long prickles: None.

Plant foliage:

*Compound leaf*.—105 mm (l)×70 mm (w).

*Quantity*.—About 4 leaves per 10 cm of stem on average.

*Leaf bearing angle to the stem*.—90 degrees.

*Color of juvenile foliage*.—Upper side: Yellow-Green Group 144A. Lower side: Yellow-Green Group 144B.

*Color of mature foliage*.—Upper side: Yellow-Green Group 146A. Lower side: Yellow-Green Group 147B.

Plant leaves and leaflets:

*Stipules*.—Size: 10 mm long, 2 mm wide. Quantity: 2 per compound leaf. Shape: Linear, slightly broad based with outward extending apices. Margins: Finely serrated. Color: Yellow-Green Group 144A.

*Petiole*.—Length: 10 mm. Diameter: 2 mm. Upper surface color: Yellow-Green Group 144A. Lower surface color: Yellow-Green Group 144B.

*Rachis*.—Length: 60 mm. Upper surface color: Yellow-Green Group 144A. Lower surface color: Yellow-Green Group 144B.

*Leaflet*.—Quantity: Normally 5 or 7 leaflets. Margins: Serrated. Size: Terminal leaflets are about 45 mm long, 25 mm wide. Shape: Generally elliptical. Base: Rounded. Apex: Mucronate. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpar137' substantially as described and illustrated herein.

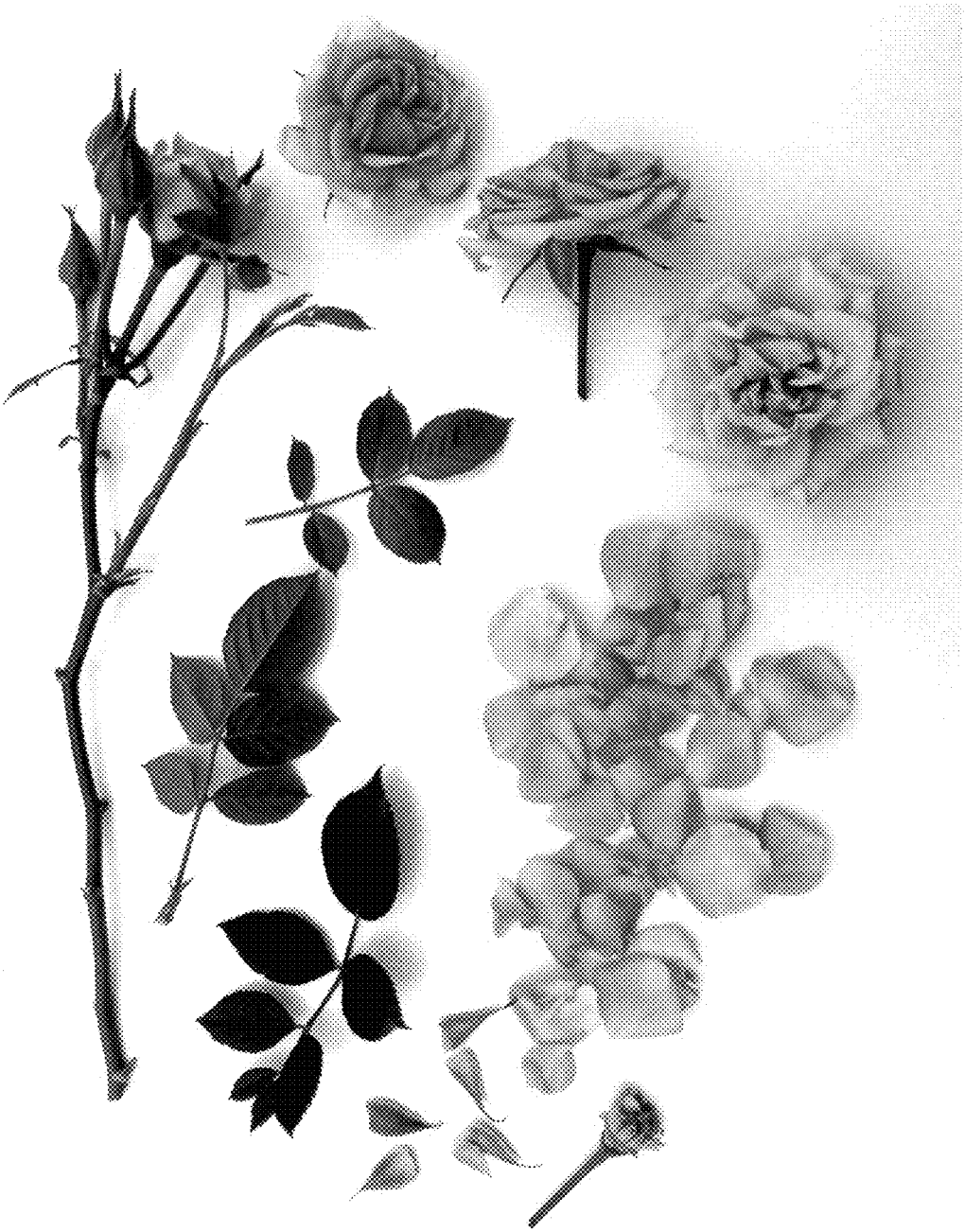

* * * * *